United States Patent

Brown et al.

[11] Patent Number: 5,886,231
[45] Date of Patent: Mar. 23, 1999

[54] PROCESS FOR THE PRODUCTION OF 2-(SUBSTITUTED BENZOYL) 1,3 CYCLOHEXANEDIONES

[75] Inventors: Stephen Martin Brown, Upper Cumberworth; Howard Rawlinson, Sowery Bridge, both of United Kingdom

[73] Assignee: Zeneca Limited, London, England

[21] Appl. No.: 860,335

[22] PCT Filed: Jan. 16, 1996

[86] PCT No.: PCT/GB96/00082

§ 371 Date: Jun. 24, 1997

§ 102(e) Date: Jun. 24, 1997

[87] PCT Pub. No.: WO96/22958

PCT Pub. Date: Aug. 1, 1996

[30] Foreign Application Priority Data

Jan. 25, 1995 [GB] United Kingdom ............... 9501434

[51] Int. Cl.[6] .................................................. C07C 45/54
[52] U.S. Cl. ........................ 568/310; 568/341; 568/388
[58] Field of Search ............................ 568/310, 341, 568/388

[56] References Cited

U.S. PATENT DOCUMENTS

| | | | |
|---|---|---|---|
| 4,695,673 | 9/1987 | Heather et al. | 568/310 |
| 4,780,127 | 10/1988 | Michaely et al. | 71/103 |
| 4,806,146 | 2/1989 | Carter | 71/98 |
| 5,468,878 | 11/1995 | Nasuno et al. | 549/23 |
| 5,480,858 | 1/1996 | Sakamoto et al. | 504/288 |

FOREIGN PATENT DOCUMENTS

| | | | |
|---|---|---|---|
| 0186117 | 7/1986 | European Pat. Off. | C07C 45/54 |
| 0186118 | 8/1987 | European Pat. Off. | C07C 79/36 |
| 0249150 | 12/1987 | European Pat. Off. | C07C 149/26 |

*Primary Examiner*—Gary Geist
*Assistant Examiner*—Sreeni Padmanabhan
*Attorney, Agent, or Firm*—Marian T. Thomson

[57] ABSTRACT

A process for preparing a compound of formula (I):

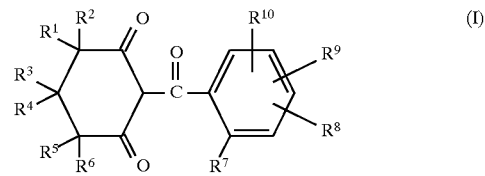

by rearrangement of a compound of formula (II):

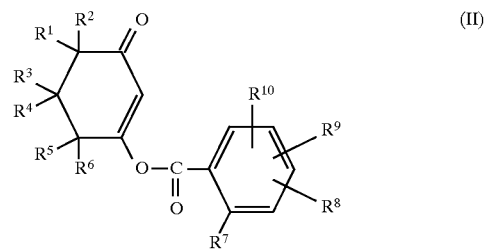

in a non-polar solvent in the presence of a cyanide source, an alkali or alkaline earth metal carbonate, a phase transfer catalyst and 1–6 moles of water with respect to the compound of formula (II).

10 Claims, No Drawings

PROCESS FOR THE PRODUCTION OF 2-(SUBSTITUTED BENZOYL) 1,3 CYCLOHEXANEDIONES

This is the U.S. National Stage Application of PCT/GB96/00082 filed Jan. 16, 1996 now WO 96/22958 published Aug. 1, 1996.

The present invention relates to the production of 2-(substituted benzoyl)-1,3-cyclohexanedione compounds.

2-(substituted benzoyl)-1,3-cyclohexanediones are known as herbicides from for example U.S. Pat. No. 4,780,127, U.S. Pat. No. 4,806,146, U.S. Pat. No. 4,946,981, U.S. Pat. No. 5,006,158, WO 9408988 and WO 9404524. One method of producing these compounds is by re-arrangement of an enol ester. This method is described in U.S. Pat. No. 4,780,127 and U.S. Pat. No. 4,695,673.

This process provides a means to obtain the desired compounds but generally employs organic bases such as triethylamine or employs polar aprotic solvents when alkali metal carbonates are used as base. The use of organic bases and polar aprotic solvents present problems on an industrial scale due to the need to recover these materials efficiently. It has surprisingly been found that non-polar solvents in combination with inorganic bases can be employed if a critical amount of water is added to the reaction medium.

According to the present invention there is provided a process for preparing a compound of formula (I) where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or RaS in which Ra is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy or substituted phenoxy; $R_bS(O)n\ Om$ in which m is 0 or 1, n is 0, 1 or 2 and Rb is $C_{1-4}$ alkyl, $C_{1-4}$ haloalkyl, phenyl or benzyl, $NHCOR_c$ in which Rc is $C_{1-4}$ alkyl, NRdRe in which Rd and Re independently are hydrogen or $C_{1-4}$ alkyl; RfC(O)— in which Rf is hydrogen, $C_{1-4}$ alkyl, $C_{1-4}$ haloalkyl or $C_{1-4}$ alkoxy; $SO_2NRgRh$ in which Rg and Rh independently are hydrogen or $C_{1-4}$ alkyl; or any two of $R^8$, $R^9$ and $R^{10}$ together with the carbon atoms to which they are attached form a 5 or 6 membered heterocyclic ring containing up to three heteroatoms selected from O, N or S and which may be optionally substituted by $C_{1-4}$ alkyl, $C_{1-4}$ haloalkyl, $C_{1-4}$ alkoxy, $=NOC_{1-4}$ alkyl or halogen; which process comprises the rearrangement of a compound of formula (II) where $R^1$, $R^2$, $R^3$, $R^4$, $R^5$, $R^6$, $R^7$, $R^8$, $R^9$ and $R^{10}$ are as defined in relation to formula (I), in a non-polar solvent in the presence of a cyanide source, an alkali or alkaline earth metal carbonate, a phase transfer catalyst and 1–6 moles of water with respect to the compound of formula (II).

As used herein the term "alkyl", refers to straight or branched chains. The term "haloalkyl" refers to an alkyl group substituted by at least one halogen. Similarly the term "haloalkoxy" refers to an alkoxy group substituted by at least one halogen. As used herein the term "halogen" refers to fluorine, chlorine, bromine and iodine.

Suitable optional substituents for phenoxy groups $R^8$, $R^9$ and $R^{10}$ include halogen such as fluorine and chlorine and $C_{1-4}$ haloalkyl.

A preferred group of compounds of formula (I) are those where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or RaS in which Ra is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy or substituted phenoxy; $R_bS(O)n\ Om$ in which m is 0 or 1, n is 0, 1 or 2 and Rb is $C_{1-4}$ alkyl, $C_{1-4}$ haloalkyl, phenyl or benzyl, $NHCOR_c$ in which Rc is $C_{1-4}$ alkyl, NRdRe in which Rd and Re independently are hydrogen or $C_{1-4}$ alkyl; RfC(O)— in which Rf is hydrogen, $C_{1-4}$ alkyl, $C_{1-4}$ haloalkyl or $C_{1-4}$ alkoxy; or $SO_2NRgRh$ in which Rg and Rh independently are hydrogen or $C_{1-4}$ alkyl.

Preferably $R^1$, $R^2$, $R^3$, $R^4$, $R^5$ and $R^6$ are independently hydrogen or $C_{1-4}$ alkyl. More preferably $R^1$, $R^2$, $R^5$ and $R^6$ are hydrogen and $R^3$ and $R^4$ are independently hydrogen or methyl.

$R^7$ is preferably halogen or $NO_2$. A preferred value for $R^8$ is hydrogen.

$R^9$ is preferably hydrogen or $C_{1-4}$ alkoxy, especially ethoxy. Most preferably $R^9$ is hydrogen.

Preferably $R^{10}$ is a group $RbS(O)_n Om$ where Rb, n and m are as defined above. More preferably m is zero, n is 2 and Rb is $CH_3$ or $C_2H_5$. Most preferably $R^{10}$ is a group $CH_3SO_2$ attached to the benzoyl group at the 4-position.

The term "cyanide source" refers to a substance or substances which under the rearrangement conditions consists of or generates hydrogen cyanide and/or cyanide anion.

Preferred cyanide sources are alkali metal cyanides such as sodium and potassium cyanide; cyanohydrins of methyl alkyl ketones having from 1–4 carbon atoms in the alkyl groups, such as acetone or methyl isobutyl ketone cyanohydrins; benzaldehyde cyanohydrin; cyanohydrins of $C_2$–$C_5$ aliphatic aldehydes such as acetaldehyde cyanohydrin, propionaldehyde cyanohydrin, etc; cyclohexaneone cyanohydrin; triethylamine-HCN complex; tetrabutyl ammonium bromide/$CN^-$ mixtures; lactonitrile; lower alkyl silyl cyanides, notably di- and tri-(lower alkyl)silyl cyanides such as dimethyl and trimethyl-silyl cyanides; potassium ferricyanide; and hydrogen cyanide itself. More preferably the cyanide source is an alkali metal cyanide most preferably sodium cyanide. The cyanide source is used in an amount up to about 50 mole percent based on the enolester. It may be used in as little as about 1 mole percent to produce an acceptable rate of reaction at about 40° C., on a small scale. Larger scale reactions give more reproducible results with slightly higher catalyst levels of about 5 mole percent. Generally about 1–10 mole % of the cyanide source is preferred.

The process is conducted with a molar excess, with respect to the enol ester compound of formula (II), of an alkali or alkaline earth metal carbonate, preferably sodium carbonate.

The alkali or alkaline earth metal carbonate is used in an amount of from about 1 to about 4 moles per mole of enol ester, preferably about 2 moles per mole.

A number of different solvents may be usable in this process, depending on the nature of the reactants. A preferred solvent for this reaction is toluene. Other solvents which may be employed, depending on the reactants or products include alkyl aromatics such as xylene, cumene, and cymene or alkanes such as hexane or cycloalkanes such as cyclohexane.

The selection of a suitable phase transfer catalyst can be determined by routine procedures well known to the skilled chemist. Known phase transfer catalysts include tetralkyl ammonium halides and phosphonium salts. Preferred catalysts are tetralkyl ammonium halides, especially tetrabutyl ammonium bromide. The phase transfer catalyst is generally used at 1–10 mol %.

Water is preferably used at 2–6, especially 4, moles per mole of enol ester.

In general, depending on the nature of the reactants and the cyanide source, the rearrangements may be conducted at temperatures from 0° C., up to about 100° C. Preferably the temperature is at a maximum of about 80° C. Most preferably the temperature is from about 20° C., to about 70° C. In some cases, for instance when there is a possible problem of excessive by-product formation (for instance, when using an orthonitro benzoyl halide) the temperature should be kept at about 40° C. maximum.

The process may be carried out using the enol ester as the starting material, or with generation of the enol ester in situ, for instance by reaction of a compound of formula (III) where $R^1$, $R^2$, $R^3$, $R^4$, $R^5$ and $R^6$ are as defined in relation to formula (I) with a compound of formula (IV) where $R^7$, $R^8$, $R^9$ and $R^{10}$ are as defined in relation to formula (I) and Z is a halo, preferably chloro.

When the enol ester is utilised as a starting material it may be prepared by any of a number of known means, including acylation of a compound of formula (III) with, a compound of formula (IV).

The production of compounds of formula (I) according to this invention, may be advantageously carried out starting with compounds of formula (III) and formula (IV) and may be carried out with or without isolation of the intermediate enol ester (II). When carried out in two steps, the compound of formula (III) and the compound of formula (IV) are reacted in the presence of a alkali or alkali earth metal carbonate.

The enol ester isolated from the resulting product mix by known techniques, for instance washing the resultant solution with acid and base, and with saturated sodium chloride solution, and drying. Such a technique is advantageous when a different solvent is preferred for the second step—the rearrangement of the enol ester to the compound of formula (I). The dried enol ester may be mixed with an appropriate solvent such as acetonitrile, 1,2-dichloroethane, or toluene and contacted with the appropriate amounts of cyanide source, phase before catalyst, sodium carbonate and water, and heated to an temperature, to produce the final product.

In a preferred alternative the enol ester may be retained in the reaction product and the second stage may be carried out (using the same solvent) by adding a cyanide source, water and additional base if necessary to produce the compound of formula (I).

Comparable yields can be obtained either with or without isolation of the enol ester.

The compound of formula (I) is obtained from this reaction in the form of its salt. The desired acylated compound of formula (I) may be obtained with acidification and extraction with an appropriate solvent.

The process of the invention is illustrated by the following example.

EXAMPLE 1

Toluene (22 g) was charged to a 4 necked 250 ml flamed dried round bottomed flask previously purged with $N_2$ and sealed to a Drierite guard tube and oil bubbler. 1,3 Cyclohexanedione (5.0 g) and sodium carbonate powder (12.0 g) were charged to give a red slurry. This mass was heated to 55°–57° C. and held for 20 minutes. 2-chloro-4-(methylsulphonyl) benzoyl chloride (11.0 g) was added to toluene (25 g) and heated to obtain a complete solution. This solution was added to the mass dropwise, via a heated dropping funnel, over 20 minutes at 55°–57° C. to give a pale yellow slurry. This mass was held at 55°–57° C. for 2 hours. Sodium cyanide (0.103 g), tetra n-butylammonium in bromide (0.13 g) and water (2.9 g) were added and the reaction held on temperature for a further three hours. A solid formed on the base of the flask which could not be agitated so the reaction mass was screened and the paste and liquors analysed. The required compound of formula (I) as the sodium salt was produced in 81.6% yield.

The above procedure was repeated but omitting the water and none of the required product was obtained.

The procedure of Example 1 was repeated a second time using 8 moles of water with respect to the enol ester and the yield of the required product was less than 1%.

CHEMICAL FORMULAE
(IN DESCRIPTION)

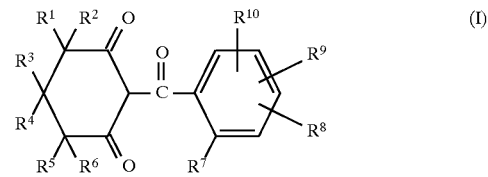

(I)

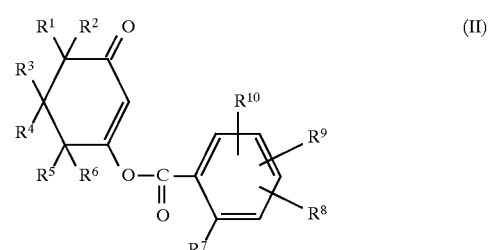

(II)

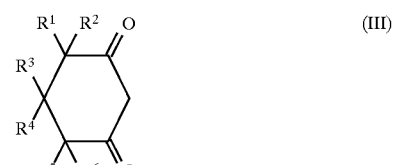

(III)

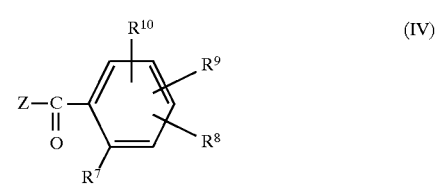

(IV)

We claim:
1. A process for preparing a compound of formula (I):

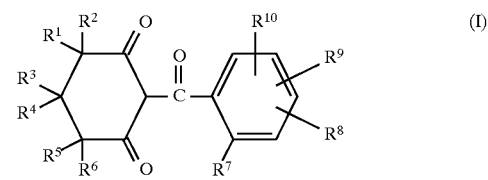

(I)

where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or RaS in which Ra is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy or substituted phenoxy; $RbS(O)_nO_m$ in which m is 0 or 1, n is 0, 1 or 2 and Rb is $C_{1-4}$ alkyl, $C_{1-4}$ haloalkyl, phenyl or benzyl, NHCORc in which Rc is $C_{1-4}$ alkyl, NRdRe in which Rd and Re independently are hydrogen or $C_{1-4}$ alkyl; RfC(O)— in which Rf is hydrogen, $C_{1-4}$ alkyl, $C_{1-4}$ haloalkyl or $C_{1-4}$ alkoxy; $SO_2NRgRh$ in which Rg and Rh independently are hydrogen or $C_{1-4}$ alkyl; or any two of $R^8$, $R^9$ and $R^{10}$ together with the carbon atoms to which they are attached form a 5 or 6 membered heterocyclic ring containing up to three heteroatoms selected from O, N or S and which may be optionally substituted by =$NOC_{1-4}$ alkyl, $C_{1-4}$ alkyl, $C_{1-4}$ haloalkyl, $C_{1-4}$ alkoxy or halogen; which process comprises the rearrangement of a compound of formula (II) where $R^1$, $R^2$, $R^3$, $R^4$, $R^5$, $R^6$, $R^7$, $R^8$, $R^9$ and $R^{10}$ are as defined in relation to formula (I), in a non-polar solvent in the presence of a cyanide source, an alkali or alkaline earth metal carbonate, a phase transfer catalyst and 1–6 moles of water with respect to the compound of formula (II):

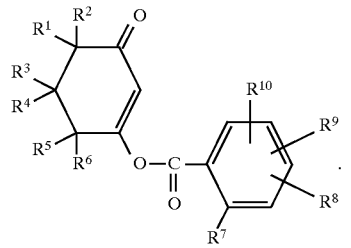

2. A process according to claim 1 where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or RaS in which Ra is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy or substituted phenoxy; $R_bS(O)n\ Om$ in which m is 0 or 1, n is 0, 1 or 2 and Rb is $C_{1-4}$ alkyl, $C_{1-4}$ haloalkyl, phenyl or benzyl, $NHCOR_c$ in which Rc is $C_{1-4}$ alkyl, NRdRe in which Rd and Re independently are hydrogen or $C_{1-4}$ alkyl; RfC(O)— in which Rf is hydrogen, $C_{1-4}$ alkyl, $C_{1-4}$ haloalkyl or $C_{1-4}$ alkoxy; or $SO_2NRgRh$ in which Rg and Rh independently are hydrogen or $C_{1-4}$ alkyl.

3. A process according to claim 1 where $R^1$, $R^2$, $R^5$ and $R^6$ are hydrogen and $R^3$ and $R^4$ are independently hydrogen or methyl.

4. A process according to claim 1 where $R^7$ is halogen or $NO_2$.

5. A process according to claim 1 where $R^8$ is hydrogen.

6. A process according to claim 1 where $R^9$ is hydrogen or $C_{1-4}$ alkoxy.

7. A process according to claim 1 where $R^{10}$ is a group $CH_3SO_2$ attached to the benzoyl group at the 4-position.

8. A process according to claim 1 where the cyanide source is an alkali metal cyanide.

9. A process according to claim 1 where the solvent is toluene.

10. A process according to claim 1 where the phase transfer catalyst is tetrabutyl ammonium bromide.

* * * * *